US011167883B1

(12) United States Patent
Schuldt

(10) Patent No.: US 11,167,883 B1
(45) Date of Patent: Nov. 9, 2021

(54) INVENTORY MANAGEMENT SYSTEM

(71) Applicant: Eric Schuldt, Livonia, MI (US)

(72) Inventor: Eric Schuldt, Livonia, MI (US)

( * ) Notice: Subject to any disclaimer, the term of this patent is extended or adjusted under 35 U.S.C. 154(b) by 0 days.

(21) Appl. No.: 17/247,187

(22) Filed: Dec. 3, 2020

Related U.S. Application Data

(60) Provisional application No. 63/017,176, filed on Apr. 29, 2020.

(51) Int. Cl.
*B65D 25/06* (2006.01)
*A47F 5/00* (2006.01)
*G06Q 10/08* (2012.01)
*G16H 40/20* (2018.01)

(52) U.S. Cl.
CPC .............. *B65D 25/06* (2013.01); *A47F 5/005* (2013.01); *A47F 5/0018* (2013.01); *G06Q 10/087* (2013.01); *G16H 40/20* (2018.01)

(58) Field of Classification Search
CPC ........ B65D 25/06; A47F 5/0018; A47F 5/005; G06Q 10/087; G16H 40/20
USPC ............ 248/235, 239, 240, 240.1, 241, 249; 211/10, 85.4, 85.13, 36, 38, 90.01, 90.02, 211/90.03, 95, 96, 119.003, 144, 134, 211/153, 149, 184
See application file for complete search history.

(56) References Cited

U.S. PATENT DOCUMENTS 2,586,005 A * 2/1952 Colonna ............... A47L 15/501 220/487
3,625,371 A * 12/1971 Dill .......................... A47F 5/01 211/153
3,750,894 A * 8/1973 Jensen .................... A47F 5/005 211/184
3,929,248 A * 12/1975 Morrison ................. A47F 5/01 220/486
4,190,167 A * 2/1980 Wells ...................... A47F 5/005 108/61
5,103,987 A * 4/1992 Davis ..................... A47B 65/20 211/43
5,381,908 A * 1/1995 Hepp .................. A47B 57/585 108/61
5,690,038 A * 11/1997 Merit ...................... A47F 5/005 108/60
6,142,317 A * 11/2000 Merl ....................... A47F 1/125 211/184
6,382,431 B1 * 5/2002 Burke ..................... A47F 1/126 211/184

(Continued)

*Primary Examiner* — Christopher Garft
*Assistant Examiner* — Michael McDuffie
(74) *Attorney, Agent, or Firm* — University of Michigan Law School

(57) ABSTRACT

A coupling mechanism which supports an inventory divider within a storage bin. The coupling mechanism comprises a joint extension and a holding mechanism. The coupling mechanism is coupled to an interior wall of a supply bin. An inventory divider is inserted into the joint extension and is rotated within the joint extension between and upper and lower position within the storage bin. The holding mechanism of the coupling mechanism retains the inventory divider in the upper position, dividing the storage bin into two compartments. By retaining the inventory divider with a holding mechanism that is not directly connected to the bin, the wear on the holding mechanism is substantially reduced and the inventory divider is more secure.

13 Claims, 7 Drawing Sheets

(56) References Cited

U.S. PATENT DOCUMENTS

| | | | | |
|---|---|---|---|---|
| 7,198,340 | B1 * | 4/2007 | Ertz | F25D 25/02<br>211/119.003 |
| 7,441,663 | B2 * | 10/2008 | Osborn | B07C 3/008<br>206/561 |
| 7,950,537 | B1 * | 5/2011 | Goodman | A47B 57/581<br>211/184 |
| 8,123,185 | B2 * | 2/2012 | Winig | A47B 57/408<br>248/250 |
| 8,701,898 | B2 * | 4/2014 | Chai | A47L 15/504<br>211/41.6 |
| 8,938,396 | B2 * | 1/2015 | Swafford, Jr. | A47F 1/126<br>705/22 |
| 9,326,604 | B1 * | 5/2016 | Schuldt | A47B 57/581 |
| 10,482,423 | B1 | 11/2019 | Willit et al. | |
| 2003/0037712 | A1 * | 2/2003 | Welch | A47B 57/58<br>108/180 |
| 2003/0189018 | A1 * | 10/2003 | Hopkins | A47F 5/01<br>211/90.02 |
| 2007/0023374 | A1 * | 2/2007 | Nawrocki | A47F 5/0846<br>211/90.01 |
| 2009/0248198 | A1 * | 10/2009 | Siegel | G06Q 10/08<br>700/231 |
| 2011/0290804 | A1 * | 12/2011 | Kohles | A47L 15/505<br>220/488 |
| 2014/0138330 | A1 * | 5/2014 | Hardy | A47B 57/588<br>211/59.3 |
| 2014/0319087 | A1 * | 10/2014 | Sosso | A47F 1/126<br>211/59.3 |
| 2015/0129524 | A1 * | 5/2015 | Cushion | A61B 50/20<br>211/85.13 |
| 2020/0037784 | A1 * | 2/2020 | Padvoiskis | A47F 5/0807 |

* cited by examiner

INVENTORY MANAGEMENT SYSTEM

CROSS REFERENCE TO RELATED APPLICATIONS

This application claims priority to provisional application 63/017,176, filed on Apr. 29, 2020, which is incorporated herein by reference.

FIELD OF THE DISCLOSURE

The invention relates to an inventory management system for wire and non-wire bins; more particularly, the invention relates to a coupling mechanism for an inventory management system.

BACKGROUND OF THE DISCLOSURE

Shelving systems are used in many environments to store supplies and track the need for inventory replenishment. These multi-shelf systems can consist of many separate containers or many subdivided containers. These individual containers or container sections contain dividers to divide inventory between a front and back section, and act as indicators that supplies are running out and need to be replenished when the front section supplies are low. These systems are in particular used in hospitals to store smaller medical supplies. It is critical that inventory is replenished before it runs out, as supply order can take time to arrive and demand for supplies can rise quickly.

An object of this invention is to improve on the currently existing system, particularly with regards to the way the divider is held up. A related system, outlined in U.S. Pat. Nos. 9,326,604 and 10,482,423, assigned to LogiQuip, LLC, Galesburg, Mich., describes an inventory system for wire baskets or shelves that utilizes plastic clips attached to the base of a wire container to hold the divider up until it is rotated down. The clips are pivotally coupled directly to the base of the wire storage container to allow for direct pivotal movement of the inventory divider relative to the container. This direct pivotal interaction results in progressive wear and tear of the clips and the dividers after repeated use because the clips and inventory dividers are plastic while the container mesh is metal. The resulting deterioration of the coupling mechanism can result in difficulty maintaining the inventory divider in an upright position and requires more frequent replacement. In addition, this currently available model is designed to interact only with wire mesh containers, as the clips must be attached to the wire of the container; this makes it difficult to adapt the system to existing storage bins having non-wire mesh walls and bases. Thus, an improved system that utilizes a coupling mechanism that is durable and does not undergo direct wear and tear between wire and plastic, is easily detachable for efficient use of storage space, and may be adapted for use in different types of storage containers is desirable.

SUMMARY OF THE DISCLOSURE

At least one embodiment relates to an inventory management system. The inventory management system includes an inventory divider pivotally coupled to a pair of coupling mechanisms within a storage container. The coupling mechanism is configured to be detachably coupled to the storage container at a fixed position relative to the storage container. The coupling mechanism includes a back face. The back face includes a plurality of attachment clips for detachably coupling the coupling mechanism to a wall of the storage container. The coupling mechanism includes a front face. The front face includes a holding mechanism for detachably coupling a portion of the inventory divider to the coupling mechanism, so as to orient and hold the inventory divider in an upright position in the storage container. The front face further includes an extension for pivotally coupling the inventory divider to the coupling mechanism. The inventory divider separates a container so that supplies may be stored in front of the divider and behind the divider. The inventory divider can be selectively detached from the holding mechanism and pivoted about an axis defined by the extension, so that the inventory divider can provide a visual indication of a need for replenishing inventory in the container. The inventory divider can also be selectively removed from the extension of the coupling mechanism. In this manner, the disclosed inventory management system provides for a robust interface between the inventory divider and the container, allows for easy replacement of various components of the system, and allows for reconfiguration of a storage area.

DETAILED DESCRIPTION OF PREFERRED EMBODIMENTS

Figure 1:
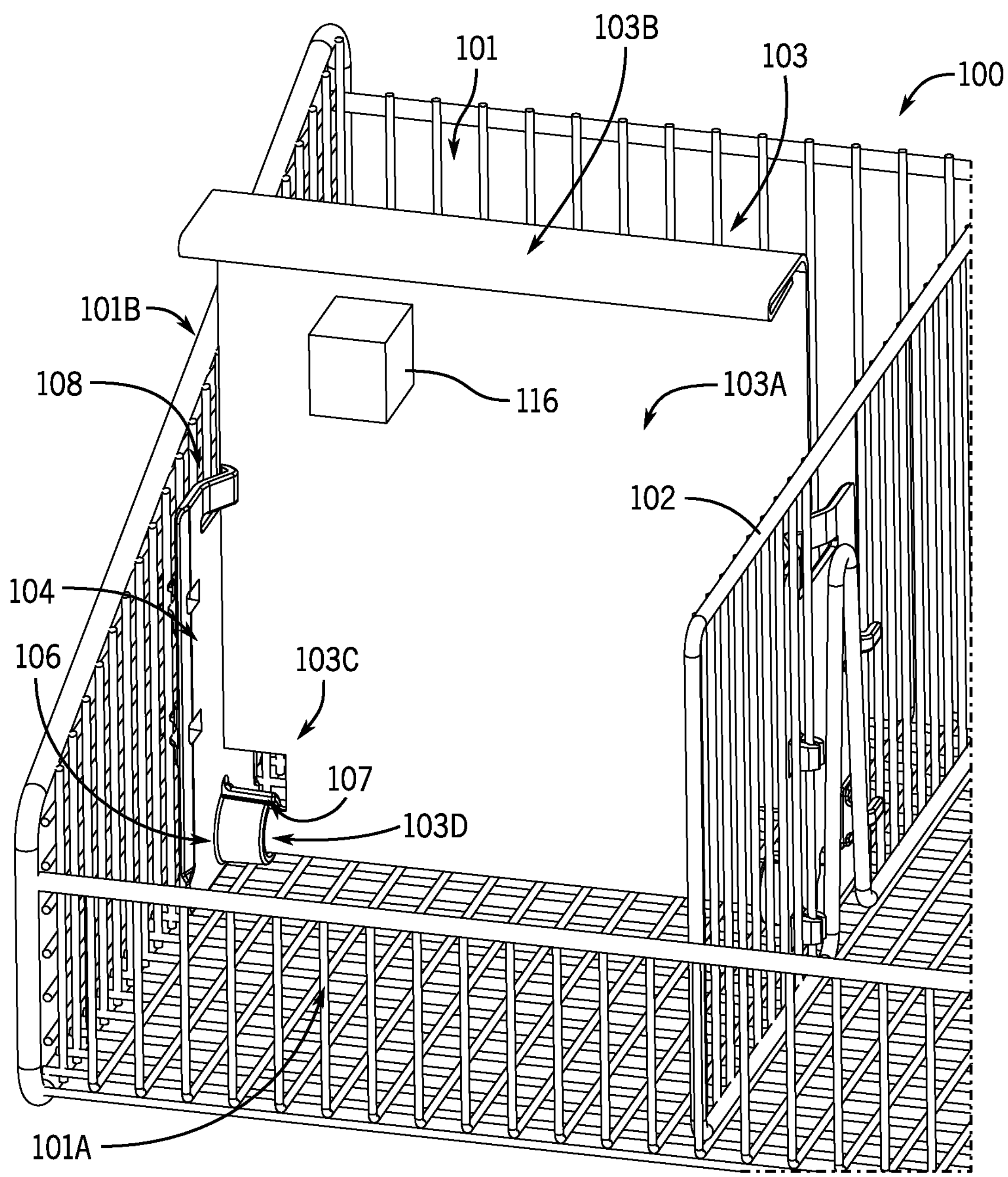
FIG. 1 is a perspective view of an inventory management system according to an exemplary embodiment.

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

Generally speaking, inventory management systems are used in many different environments, such as in healthcare. These inventory management systems typically include multiple open-ended storage containers or bins either placed on shelving units or attached to walls to define separate storage areas. In the healthcare industry, for example, such systems are utilized for storage and inventory management of medical supplies. These types of systems may include a movable inventory divider (e.g., Kanban divider, etc.) having a label to provide a visual indication that supplies contained in a particular storage area or container are low and need to be replenished. For example, when supplies in a particular container are running low, the inventory divider can be manually moved (e.g., pivoted) by a user, such that the label indicating the low quantity is clearly visible to a person trying to access the container, so that the supplies can be replenished. These inventory management systems can undergo a significant amount of wear due to rapidly changing quantities of medical supplies in a healthcare environment. Thus, the use of robust and easily detachable inventory dividers in such environments is desirable.

Currently available inventory management systems utilize inventory dividers that are defined by clear plastic flange dividers, which are usually coupled to a wire mesh storage container by a separate coupling mechanism. These coupling mechanisms are typically pivotally coupled directly to the base of the storage container, such as along a wire mesh rail of the container, so as to allow for direct pivotal movement of the inventory divider relative to the container. Such direct pivotal interaction, however, can result in progressive wear of the coupling mechanisms and the inventory dividers after repeated use, since the containers are typically made of metal (e.g., metal wire mesh) and the coupling mechanisms/inventory dividers are made of plastic. The resulting deterioration of the coupling mechanism can result in difficulty maintaining the inventory divider in an upright position. Additionally, currently available coupling mechanisms are designed to only interact with wire rails of wire mesh containers, thereby making it impractical to incorporate inventory dividers in storage systems with storage bins having non-wire mesh walls and bases. Accordingly, a system that provides for a coupling mechanism and inventory divider that is durable, easily detachable so as to permit efficient usage of storage space and may be adapted for use in different types of storage containers is desirable.

Referring generally to the FIGURES, disclosed herein are inventory management systems that include coupling mechanisms (i.e., 104, 201) that can be coupled to a storage container. The coupling mechanisms include an integrated joint extension 106 having a unique structural design for pivotally coupling an inventory divider to the storage container. The integrated joint and the inventory divider are each designed to help minimize wear between the two components during pivotal movement of the inventory divider. The disclosed coupling mechanisms do not move or pivot relative to the container itself, unlike conventional inventory management systems. In this manner, the disclosed coupling mechanisms are more durable than conventional coupling mechanisms.

In addition, the disclosed coupling mechanisms include features that can facilitate easy removal and repositioning/replacement of the inventory divider. The disclosed coupling mechanisms may also include features that can facilitate use of the coupling mechanism with different types of storage containers, including wire mesh and non-wire mesh containers. These and other advantageous features will become apparent to those reviewing the present disclosure.

Figure 2:
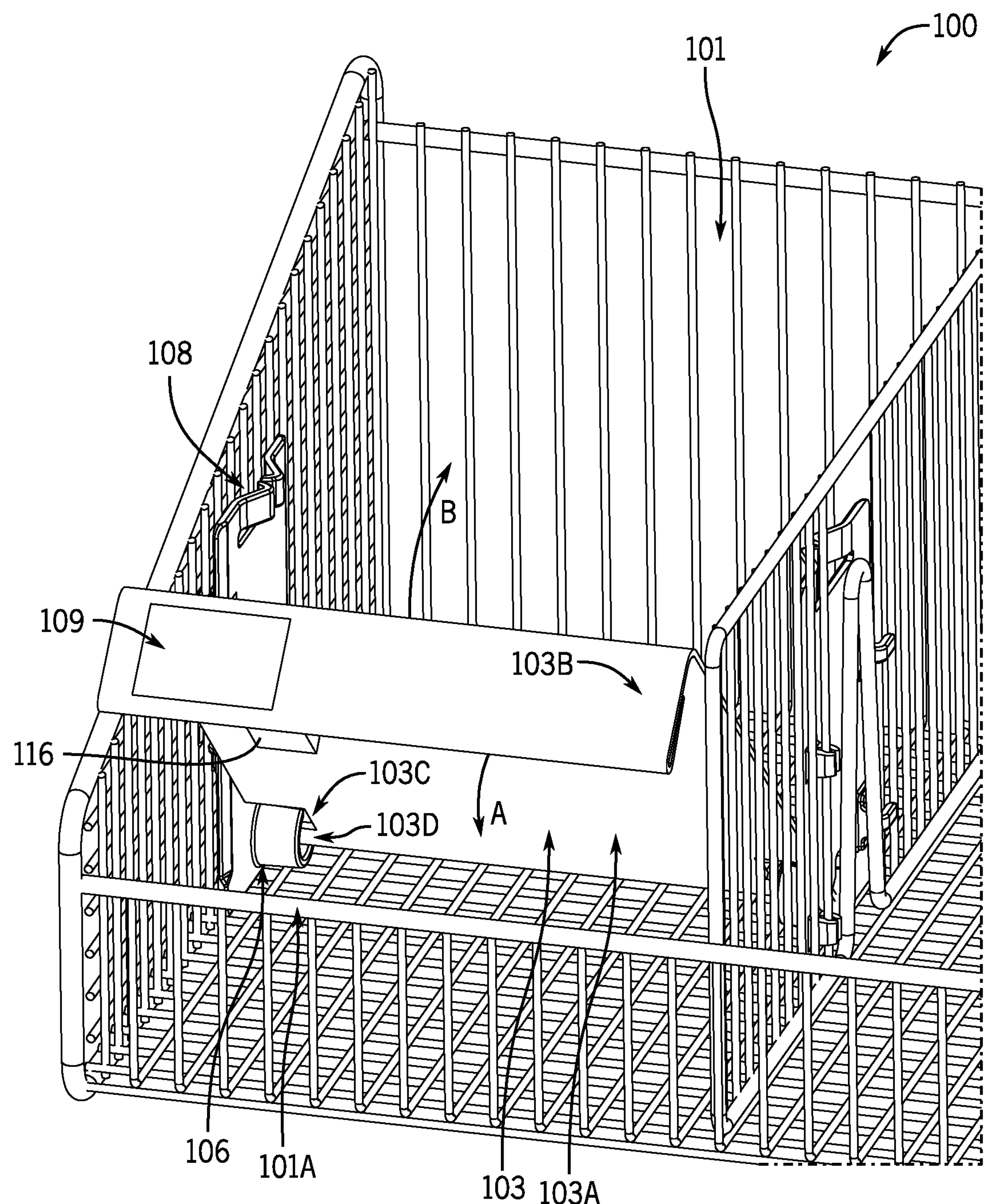
FIG. 2 is a perspective view of an inventory divider in the inventory management system of FIG. 1 shown pivoted into a lowered position.
Figure 3:
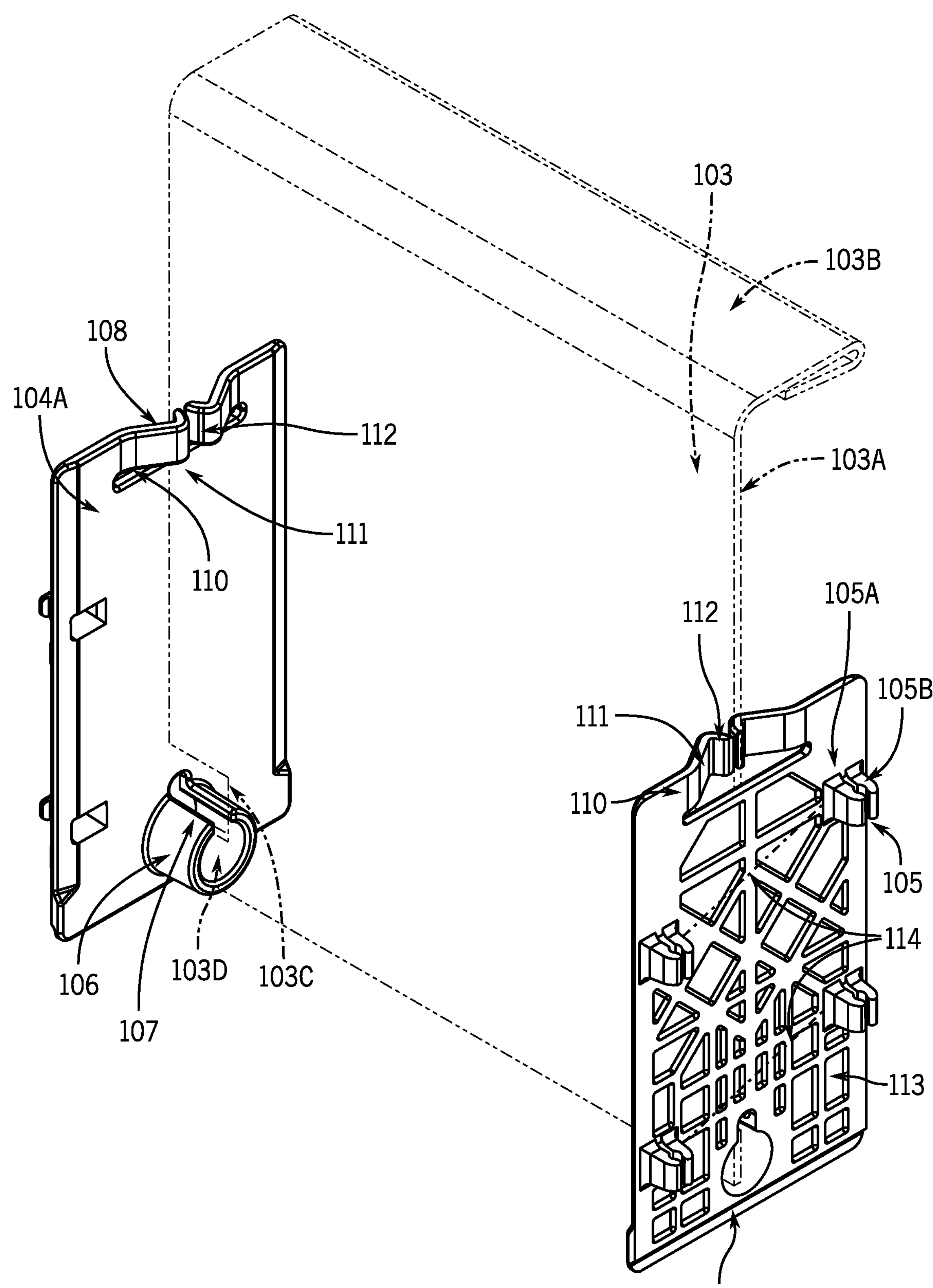
FIG. 3 is a perspective view of an exemplary embodiment of the coupling mechanism of FIG. 1.

Referring to FIGS. 1-3, an inventory management system 100 is shown according to an exemplary embodiment. The inventory management system 100 includes a storage container, shown as an open-ended wire mesh storage container 101, which can be placed on a shelving unit or coupled to a building wall via an attachment system. One or more detachable wire mesh interior divider walls 102 are coupled in the open-ended wire mesh storage container 101 to define separate storage areas or compartments of the system. An inventory divider 103 is pivotally coupled to the container 101 by a pair of coupling mechanisms 104. The coupling mechanisms 104 may be coupled to any storage container wall. These storage container walls may include interior divider walls 102 or exterior sidewalls 101B of the open-ended wire mesh storage container 101, and a set of coupling mechanism may be coupled to any combination of interior divider walls and exterior sidewalls in the following discussion of the inventory management systems 100 and 200.

According to an exemplary embodiment, the system 100 is configured to create a subdivided storage area that can allow a user to place a specific class of articles within the subdivided storage area. The size of the storage areas can be easily adjusted depending on where along the exterior sidewall 101B or detachable wire mesh interior divider wall 102 the user wishes to attach the coupling mechanisms 104, which will adjust a relative position of the inventory divider 103 in the storage area. Additionally, the subdivided storage area of the system 100 is configured to be easily adjusted in terms of width depending on the width of the particular inventory divider 103 a user chooses to selectively couple to the coupling mechanisms 104. In addition, the distance between two detachable interior divider walls 102 or the distance between an interior divider wall 102 and an exterior sidewall 101B may also be adjusted to change the width of a particular storage area.

Still referring to FIGS. 1-3, each coupling mechanism 104 includes a panel having a front face 104A and an opposite back face 104B. The coupling mechanism 104 is configured such that the front face 104A faces toward an interior of a subdivided storage compartment and the back face 104B faces toward an interior divider wall 102. The coupling mechanism 104 includes a pair of holder clips 108 positioned adjacent each other at an upper portion of the front face 104A. The holder clips 108 are configured to detachably couple to a portion of an inventory divider 103, so as to hold the inventory divider 103 in an upright position in the storage container. The coupling mechanism 104 further includes an integrated joint extension 106 extending axially away from the front face 104A at a lower portion of the coupling mechanism 104. The integrated joint extension 106 defines a pivot joint for pivotally coupling the inventory divider 103 to the coupling mechanism 104. The holder clips 108 and the integrated joint extension 106 each protrude outwardly from the front face 104A.

Four attachment clips are disposed on the back face 104B of the coupling mechanism 104 for detachably coupling the coupling mechanism 104 to the container. Attachment clips encompass the attachment jaw 105 embodiment in FIG. 3 as well as the attachment hook 115 embodiment in FIG. 4. In the exemplary embodiment shown in FIG. 3, the attachment jaws 105 are positioned with two attachment jaw sets oriented lengthwise at each of an upper portion and at a bottom portion of the coupling mechanism 104 on each side of the coupling mechanism 104. The positions of the attachment jaws 105 may be offset from each other to facilitate a more robust attachment to the storage container. According to an exemplary embodiment, the top and bottom pairs of attachment clips are configured such that an offset angle 114 is the same for both the top and bottom pairs of attachment jaws 105. Although the back face 104B is shown with four attachment jaws 105, it should be appreciated that more or fewer than four attachment jaws 105 may be used, according to other exemplary embodiments. The attachment jaws 105 may be located at different positions on the coupling mechanisms 104 than what is shown in the embodiment of FIG. 3. The attachment jaws 105 may be coupled to, or integrally formed with, the coupling mechanism 104.

According to an exemplary embodiment, the attachment jaws 105 of each coupling mechanism 104 can be coupled to a vertical length of wire of detachable interior divider wall 102, such that the two coupling mechanisms 104 are coupled to two separate interior divider walls 102 with the front faces 104A facing each other. Each attachment jaw 105 comprises jaw support base 105A that couples to the back face 104B of the coupling mechanism 104. A pair of jaw protrusions 105B protrude horizontally relative to the back face 104B from the jaw support base 104A to couple to a vertically running length of wire within an interior divider wall 102 or exterior sidewall 101B of the container. According to an exemplary embodiment, the offset angles 114 are configured such that two coupling mechanisms 104 can couple to the opposite face of a exterior sidewall 101B or interior divider wall 102 at the same location relative to the front end vertical wall 101A. Other embodiments of the coupling mechanism 104 may lack the attachment jaws 105 altogether, so as to allow for the coupling mechanism 104 to be coupled to non-wire mesh exterior sidewalls or detachable interior divider walls (e.g., solid plastic walls, etc.). The coupling mechanisms 104 of such embodiments could be coupled using different attachment features (e.g., adhesive material placed on the vertical side walls, etc.) and fulfill the same functions of the disclosed system 100.

Figure 4:
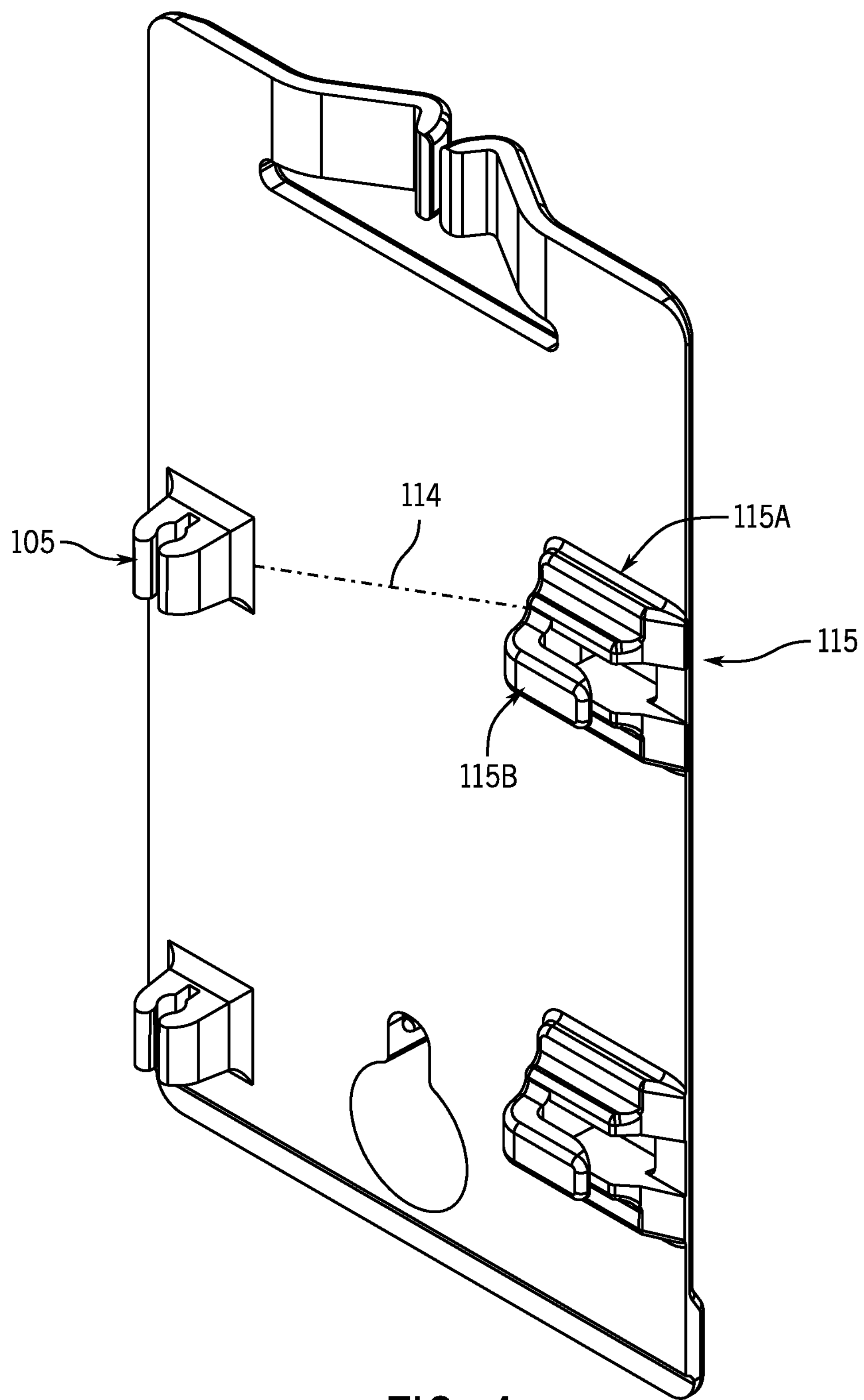
FIG. 4 is a perspective view of the back face of a coupling mechanism according to another exemplary embodiment.

According to an exemplary embodiment shown in FIG. 4, the back face 104B can be coupled to the interior divider wall 102 by attachment jaws 105 on one side of the back face 104B, and attachment hooks 115 on the other side of the back face 104B. Each attachment hook 115 comprises a hook support base 115A that couples to the back face 104B of the coupling mechanism 104. A curved head 115B protrudes horizontally from the hook base 115A relative to the back face 104B and curves at a 900 angle toward the edge of the back face 104B. The attachment hook 115 is configured so that the coupling mechanism 104 can be coupled to an interior divider wall with irregular wire spacing.

According to the exemplary embodiment shown in FIG. 3, the back face 104B of the coupling mechanism 104 includes intersecting structural embossments 113, configured such that a series of intersecting lines of raised plastic coupled to the back face 104B of the coupling mechanism 104 form a grid-like pattern. The intersecting structural embossments 113 can provide increased structural support to the coupling mechanism 104. According to an exemplary embodiment, the coupling mechanism 104 may be a molded article made from a polymeric material or combinations of polymeric materials.

As shown in the embodiment of FIGS. 1-3, the front face 104A includes a pair of holder clips 108 at an upper portion of the coupling mechanism 104 relative to the base of the storage container 101. The holder clips 108 are configured to detachably couple the inventory divider 103 to the coupling mechanism 104, so as to hold the inventory divider 103 in an upright, "resting" position. An integrated joint extension 106 is located at a lower portion of the coupling mechanism 104 relative to the base of the storage container 101. The integrated joint extension 106 has a hollow cylindrical shape that defines a pivot axis or pivot joint for pivotally coupling the inventory divider 103 to the coupling mechanism 104. The inventory divider 103 can be selectively detached from the holder clips 108 and pivoted relative to the coupling mechanism 104 via the integrated joint extension 106 either along forward rotational path A or along reverse rotational path B, as shown in FIG. 2.

As shown in the embodiment of FIG. 3, each holder clip 108 comprises a base portion 110 at the coupling mechanism 104, a lead-in surface 111 extending from the base portion 110 and outwardly away from the front face 104A at an acute angle (e.g., 30°, 45°, etc.), and a projection 112 extending from the lead-in surface 111 at its terminal end. The projection 112 protrudes inwards towards the front face 104A at an angle that intersects with the angle of the lead-in surface 111, and may terminate at a curved or beveled edge, so as to more easily clasp onto an inventory divider 103. The holder clips 108 are configured such that the projections 112 face one another and the base portions 110 are equidistant widthwise from the edges of the coupling mechanism 104. The inventory divider 103 can be detachably coupled in a space defined between the adjacent projections 112 on the coupling mechanism 104 to hold the inventory divider 103 in an upright position. Each of the holder clips 108 is configured to deflect inwardly toward the front face 104A when the inventory divider 103 is selectively pivoted away from the upright position, such as along the forward rotational path A. Likewise, when the inventory divider 103 is returned to the upright position along the reverse rotational path B, the inventory divider 103 will cause one of the holder clips 108 to deflect inwardly toward the front face 104A until the inventory divider 103 reaches the space between the adjacent projections 112, at which point the deflected holder clip 108 will return to its original position, so as to retain the inventory divider 103 between the two adjacent projections 112.

Still referring to FIG. 3, the integrated joint extension 106 is located at a lower portion of the coupling mechanism 104 relative to the base of the open-ended storage container 101. As shown in FIG. 3, the integrated joint extension 106 has a hollow cylindrical shape and extends relatively perpendicularly outward from the front face 104A. The integrated joint extension 106 includes an insertion slot 107 that extends along a top portion of the extension 106 from the front face 104A through an outermost end of the integrated joint extension 106. The insertion slot 107 can, advantageously, allow for inserting and removal of the inventory divider 103 from the integrated joint extension 106.

Still referring to FIGS. 1-3, once the attachment clips 105 couple the two coupling mechanisms 104 to two opposing interior divider walls 102 (or an interior divider wall 102 and a exterior sidewall 101B), which define the boundary width of a subdivided storage area of the disclosed system 100, an inventory divider 103 may be coupled to the two coupling mechanisms 104 by inserting a lower portion of the inventory divider 103 into the insertion slots 107 of each coupling mechanism 104 to pivotally couple the inventory divider 103 to the integrated joint extensions 106. The inventory divider 103 may also be detachably coupled to the coupling mechanisms 104 between the holder clips 108 of each coupling mechanism, so as to orient and hold the inventory divider 103 in an upright position relative to the storage area.

According to the exemplary embodiment shown in FIGS. 1-3, the inventory divider 103 includes a planar portion 103A and a flange portion 103B coupled to or integrally formed at an upper end of the planar portion 103A. The flange portion 103B is oriented substantially perpendicularly relative to the planar portion 103A. The planar portion 103A defines a pair of horizontally aligned notches 103C positioned at a lower portion of the planar portion 103A. The notches 103C define pivot arms 103D located at opposite sides of the planar portion 103A. The pivot arms 103D are configured to be inserted into the insertion slots 107 of each integrated joint extension 106, so as to pivotally couple the inventory divider 103 to the coupling mechanisms 104. The distance between the bottom end of the inventory divider 103 and the bottom edge of the pivot arm 103D (both relative to the base of the storage container 101) is slightly less than the diameter of the inner opening of the integrated joint extension 106, so as to permit rotational movement of the inventory divider 103 relative to the coupling mechanism 104. The length of the notches 103C is also greater than or equal to the length of the integrated joint extension 106.

The inventory divider 103 can directly interact with the coupling mechanism 104 at the holder clips 108 and the integrated joint extension 106. A label 109 can be attached to the exterior face of the flange portion 103B, so as to allow a user to easily discern that the contents of a subdivided storage area in the disclosed system 100 require restocking. According to an exemplary embodiment, an indicator (e.g., an adhesive label, bar code, etc.) describing to a user the contents of a subdivided storage area may also be included either on the exterior face of the flange portion 103B or on the outward face of the front-end vertical wall 101A. Additionally, the disclosed system 100 may be incorporated within a digital inventory management system configured such that information relating to the stored inventory for specific articles would be collected and processed within a central data hub. An electronic sensor 116 may be attached to the a face of the inventory divider 103 so as to relay the amount of stored inventory within the subdivided storage area to a central data hub, and relaying an alert when the amount of said stored inventory falls below a predetermined level selected by the user. The inventory divider 103 may be made from a transparent polymeric material, so as to allow for visibility through the divider of the contents in a particular storage area.

The operation of the inventory management system 100 will now be described with reference to FIGS. 1-3. In a resting, upright position of the inventory divider 103 shown in FIG. 1, the subdivided storage area (i.e., the area of the storage container 101 that can be bound by a set of interior divider walls 102, a front-end vertical wall 101A, and the inventory divider 103) of the disclosed system 100 is configured so that a user may selectively empty or fill a predetermined class of items therein. A user may adjust the location of the inventory divider 103 on the interior divider walls 102 (or exterior sidewall 101B and interior divider wall 102) relative to the front-end vertical wall 101A, such that the subdivided storage area may represent a desired proportion of the storage area (e.g., 50%, 60%, etc.) by selectively moving the coupling mechanisms 104 to a different location on the interior divider walls 102.

When a user wishes to utilize the subdivided storage area, a user may place a desired amount of inventory within the subdivided storage area and in the portion of the subdivided storage area between the inventory divider 103 and the rear wall of the subdivided storage container 101. The inventory placed in the latter category may be utilized as a reserve inventory stock that can be used after the inventory stock in the subdivided storage area has been exhausted, but before a user has replenished such stock.

When a user determines that the inventory stored within a subdivided storage area is below a desired level, the user can manually pivot the inventory divider 103 along the forward rotational path A from an upright position shown in FIG. 1 to a lowered position shown in FIG. 2. In the tilted position shown in FIG. 2, the inventory divider 103 may be configured such that the top edge of the flange portion 103B may rest on the top edge of the front-end vertical wall 101A when the level of stored inventory is empty or low, such that the label 109 is visible to a user to indicate that the inventory needs to be replenished or restocked. A user may pivot the inventory divider 103 from the upright position by exerting a sufficient force upon the flange portion 103B such that each projection 112 on the holder clips 108 deflects toward the front face 104A. When the holder clip 108 deflects a sufficient distance such that the projection 112 on the front holder clip 108 is no longer in direct contact with the inventory divider 103, the inventory divider 103 has been released. When the inventory divider 103 has been released from between the adjacent holder clips 108, the inventory divider 103 can be pivoted along the forward rotational path A, such that the pivot arms 103D will pivot within the integrated joint extensions 106 until the top edge of the inventory divider 103 directly contacts the top edge of the front-end vertical wall 101A.

After a user has replenished the inventory within a subdivided storage area, the user can manually move the inventory divider 103 along the reverse rotational path B from the tilted position shown in FIG. 2 to the upright position shown in FIG. 1 such that the inventory divider 103 comes into direct contact with the front holder clip 108. When the inventory divider 103 comes into contact with the front holder clip 108, the base 110 of the clip deflects toward the front face 104A, so that the lead-in surface 111 and projection 112 correspondingly deflect toward the front face 104A. When the inventory divider 103 comes into contact with the back holder clip 108 which faces the front holder clip 108 on the coupling mechanism 104, the inventory divider 103 will be retained in the space between the adjacent projections 112 at the upright position shown in FIG. 1. In this way, the inventory divider 103 and the coupling mechanism 104 do not directly rotationally contact the container (e.g., interior divider walls 102), thereby providing for a more robust interface, as compared to some conventional inventory management systems.

Figure 5:
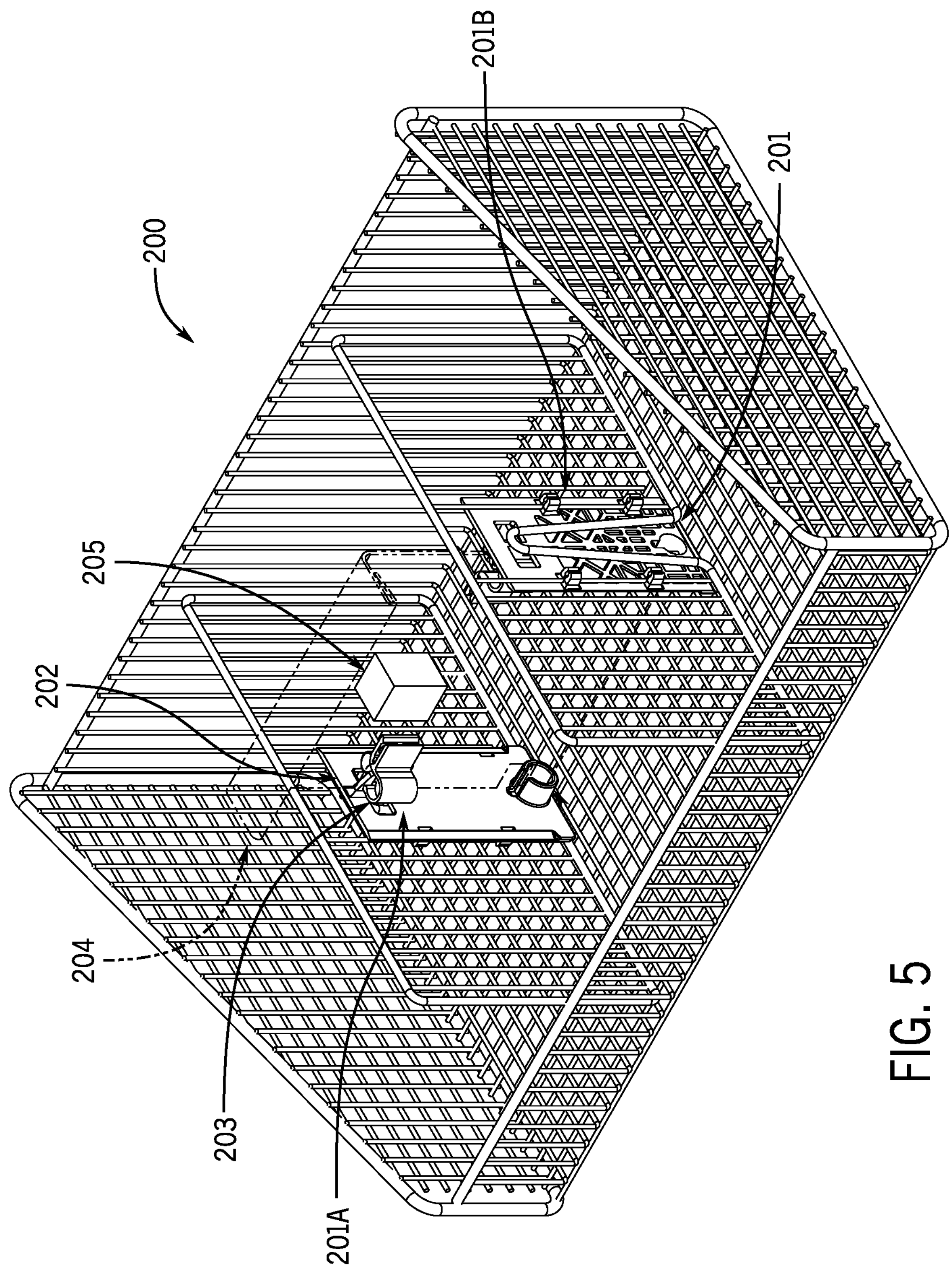
FIG. 5 is a perspective view of an inventory management system according to another exemplary embodiment.
Figure 6:
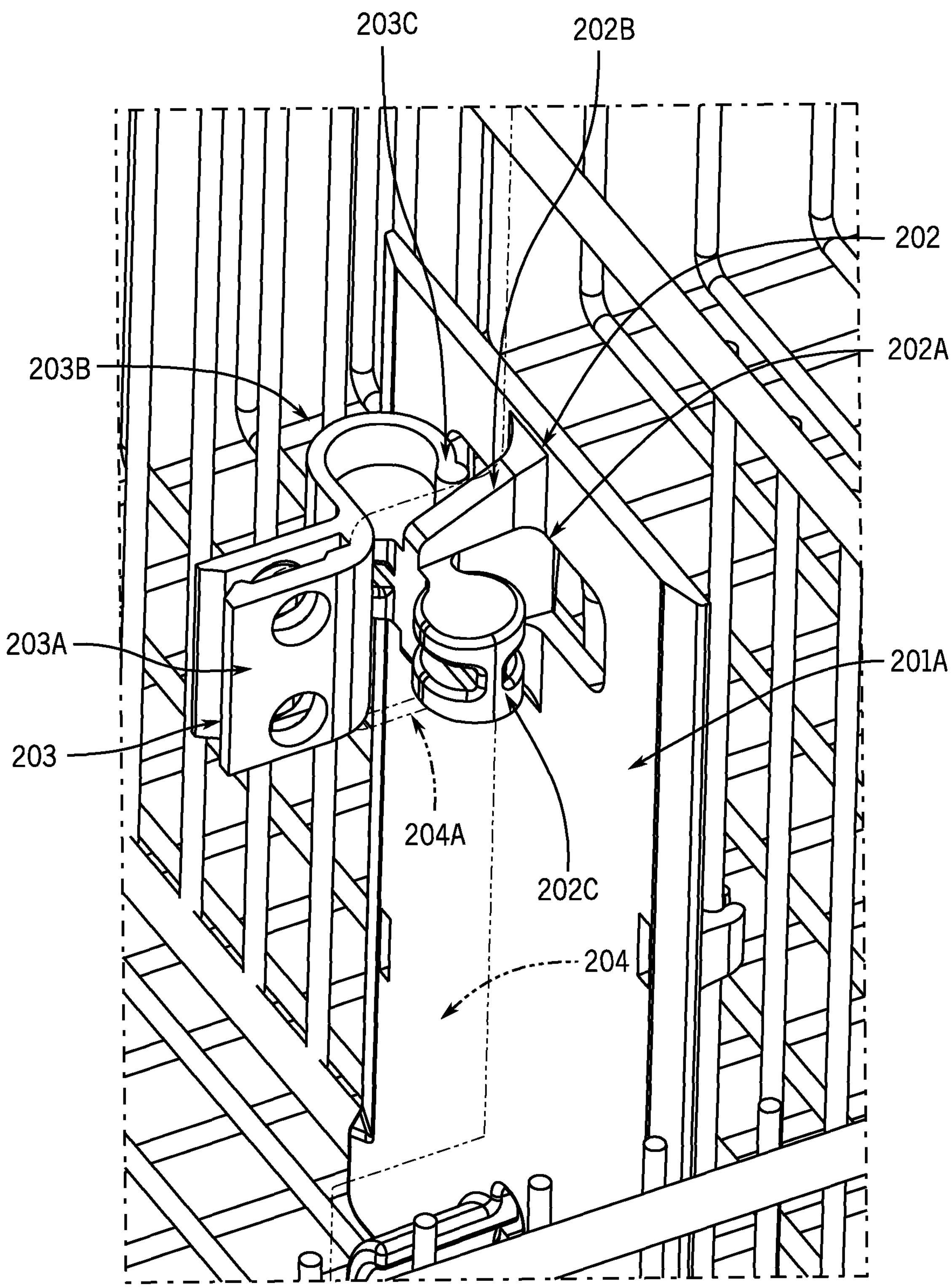
FIG. 6 is a perspective view of the coupling mechanism embodiment of FIG. 5 engaged with an inventory divider.
Figure 7:
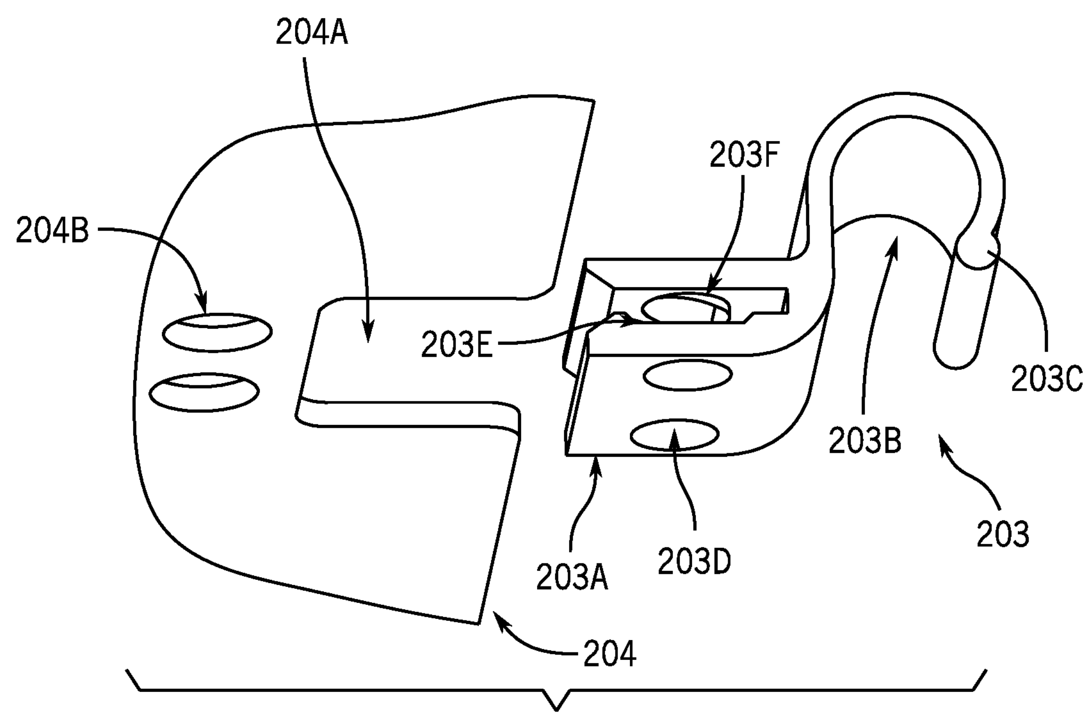
FIG. 7 is a perspective view of the detachable snap clip for the inventory divider of FIG. 6.

Referring to FIGS. 5-7, an inventory management system 200 is shown according to another exemplary embodiment. The system 200 is identical to and includes all aspects of system 100, except for the holding mechanism shown as holder clips 108 and inventory divider 103. For example, the system 200 achieves the same purpose and performs in substantially the same way as the system 100, but is configured with a different holding mechanism, shown as a retainer post 202, and inventory divider 204.

Referring to FIG. 5, the coupling mechanism 201 is shown comprising a retainer post 202 in place of the holder clips 108 shown in the system 100. The retainer post 202 serves the same purpose as the clips 108. The retainer post 202 is configured such that it protrudes perpendicularly from a front face 201A of the coupling mechanism 201. The coupling mechanism 201 includes a back face 201B that is identical to the back face 104B of the coupling mechanism 104 in system 100, but without holder clips 108. Instead, the back face 201B has a rectangular window with an arm 202A that extends perpendicularly through the middle of the rectangular window and outwardly away from the front face 201A, as shown in FIG. 6.

Still referring to FIG. 6, the retainer post 202 comprises the arm 202A, a flange 202B, and two cylindrical drum-like structures 202C. The arm 202A, a narrow vertical structure that extends vertically through the rectangular window, is coupled to or integrally formed with the retainer post 202 and coupling mechanism 201. The flange 202B is configured such that it perpendicularly protrudes from the post support. The two cylindrical drum-like structures 202C (e.g., drums, barrels, cylinders, etc.) extend outwardly from the flange 202B, one on each side of the flange 202B. Using two drum-like structures 202C, instead of one, enables the coupling mechanism 201 to be used either on the left or the right side of the inventory divider 204, although it should be appreciated that only one drum-like structure may be used, according to other exemplary embodiments. The flange 202B protrudes to a distance that enables a detachable snap clip 203 to be on substantially the same plane as the cylindrical drum-like structures 202C when the inventory divider 204 is in an upright position.

Referring to FIGS. 5-7, a pair of detachable snap clips 203 are shown coupled to each side of the inventory divider 204. According to other exemplary embodiments, the detachable snap clips 203 may be integrally formed with the inventory divider 204. In FIGS. 5-7, the detachable snap clips 203 are configured to detachably couple the inventory divider 204 to the retainer posts 202 in the upright, "resting" position shown in FIG. 6. As shown in FIG. 7, each detachable snap clip 203 comprises a base 203A and a head 203B. The base 203A includes two parallel members that define a U-shaped clip for coupling to the inventory divider 204. The base 203A is received through a notch 204A of the inventory divider 204 such that the head 203B extends in front of the inventory divider, but not outwardly past the side of the divider. The notch 204A can receive a portion of the cylindrical drum-like structures 202C therethrough, such as during pivotal movement of the inventory divider 204. The head 203B is C-shaped and is configured to detachably couple to one of the cylindrical drum-like structures 202C.

Still referring to FIG. 7, the base 203A includes one or more protrusions 203F extending inwardly within a space between the two parallel members that define the U-shaped clip. The protrusions 203F have a tapered outer surface profile (i.e., the height of the protrusion 203F increases further away from the mouth) to facilitate inserting the protrusions 203F into corresponding holes 204B of the inventory divider 204, so as to couple the detachable snap clip 203 to the inventory divider 204. Each protrusion 203F extends inwardly to define an edge or lip that is configured to engage a complementary edge of a portion of the inventory divider 204 that defines the hole 204B, so as to retain the detachable snap clip 203 on the inventory divider 204. One or more recessed portions 203D are disposed opposite to the protrusions 203F. These recessed portions 203D have substantially the same radius as those on the inventory divider 204. The inner-bottom surface of the base is structured like a wide valley with a depression 203E. The top surface of the base has two identical protrusions 203F. The two protrusions 203F have a circular cross-sectional area that is identical to holes 204B and 203D, such that the two protrusions 203F can slide into and be received within the holes 204B, thereby coupling the detachable snap clip 203 to the inventory divider 204.

The head of the clip 203B is shaped as a C-shaped hook with a radius of curvature that is substantially the same as that of the cylindrical drum-like structures 202C. The purpose of the head 203B is to be coupled to the cylindrical structure 202C by fitting around the cylindrical structure 202C to create an interference condition, so as to detachably couple the inventory divider 204 to the coupling mechanism 201. There is a circular notch 203C to secure the cylindrical structure 202C, once it is fitted inside the head 203B.

Referring to FIGS. 5-7, the inventory divider 204 in system 200 is identical to the inventory divider 103 in system 100, except for the addition of two features. First is an extra pair of horizontally aligned notches 204A that are positioned where the detachable snap clips 203 would meet the inventory divider in its upright position. Second is a pair of holes 204B, as shown in FIG. 7.

As with system 100, system 200 may be incorporated within a digital inventory management system configured such that information relating to the stored inventory for specific articles would be collected and processed within a central data hub. Within such an embodiment, an electronic sensor 205 may be attached to a face of the clear flange divider 204 so as to relay the alert when the amount of stored inventory falls below a predetermined level.

The disclosed inventory management system can, advantageously, allow for a user to easily adjust the dimensions of a subdivided storage area while reducing the rate of deterioration of the inventory divider and the coupling mechanism, so as to provide for a more robust inventory system that can reduce the frequency of replacing critical system components, as in some conventional inventory management systems.

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical or electrical.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X; Y; Z; X and Y; X and Z; Y and Z, or X, Y and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "up," "down," etc.) are merely used to describe the orientation of various elements in the FIGURES. It should be noted that the orientation of various elements may differ according to other exemplary embodiments, and that such variations are intended to be encompassed by the present disclosure.

It is important to note that the construction and arrangement of the system as shown in the various exemplary embodiments is illustrative only. Additionally, any element disclosed in one embodiment may be incorporated or utilized with any other embodiment disclosed herein. It should be appreciated that other elements of the various embodiments may be incorporated or utilized with any of the other embodiments disclosed herein.

I claim:

1. A coupling mechanism comprising:

a back face configured to couple to a storage container wall;

a front face;

an integrated joint extension protruding from the front face and configured to support an inventory divider, wherein the integrated joint extension extends substantially perpendicularly from the front face and is configured to couple the coupling mechanism to a pivot arm of the inventory divider, wherein the integrated joint extension comprises an insertion slot, and wherein the integrated joint extension is cylindrical in shape and hollow; and a holding mechanism protruding from the front face configured to secure the inventory divider in an upright position.

2. The coupling mechanism according to claim 1, further comprising one or more attachment clips on the back face configured to couple to the storage container wall.

3. The coupling mechanism according to claim 2, wherein the said-attachment clips are arranged in vertically offset pairs.

4. The coupling mechanism according to claim 2, wherein each of the attachment clips comprises one or more attachment jaws comprising:

a jaw support base coupled to the back face of the coupling mechanism; and one or more jaw protrusions that protrude outwardly from the jaw support base and are configured to engage a wire storage container wall.

5. The coupling mechanism according to claim 2, wherein the attachment clips comprise one or more attachment hooks comprising:

a hook base coupled to the coupling mechanism; and a curved head protruding from the hook base and curving toward the edge of the coupling mechanism, and configured to engage a wire storage container wall.

6. The coupling mechanism according to claim 2, wherein the attachment clips comprise attachment jaws comprising:

a jaw support base coupled to the back face of the coupling mechanism;

one or more jaw protrusions that protrude outwardly from the jaw support base and are configured to engage a wire storage container wall; and attachment hooks comprising:

a hook base coupled to the coupling mechanism; and a curved head protruding from the hook base and curving toward the edge of the coupling mechanism, and configured to engage a wire storage container wall;

wherein the attachment jaws and attachment hooks are arranged in pairs, each pairing having one attachment hook and one attachment jaw offset vertically.

7. The coupling mechanism according to claim 1, wherein the back face comprises structural embossments configured to add structural integrity to the coupling mechanism.

8. A coupling mechanism comprising:

a back face configured to couple to a storage container wall;

a front face;

an integrated joint extension protruding from the front face and configured to support an inventory divider; and a holding mechanism protruding from the front face configured to secure the inventory divider in an upright position, wherein the holding mechanism comprises holder clips that resiliently deflect inwardly toward the front face of the coupling mechanism when the divider is pivoted into the upright position and are configured to hold the inventory divider in the upright position.

9. The coupling mechanism of claim 8, wherein the holder clips comprise:

a base portion coupled to the front face;

a lead-in surface extending outwards from the base portion at an acute angle; and a projection extending from the lead-in surface at its terminal end inwards towards the front face.

10. A coupling mechanism, comprising:

a back face configured to couple to a storage container wall;

a front face;

an integrated joint extension protruding from the front face and configured to support an inventory divider; and a holding mechanism protruding from the front face configured to secure the inventory divider in an upright position, wherein the holding mechanism comprises:

a retainer post;

a flange attached to the retainer post extending outward from the front face; and at least one cylindrical structure that protrudes from the flange.

11. The coupling mechanism according to claim 10, wherein the holding mechanism is configured to engage with a detachable snap clip detachably coupled to the inventory divider.

12. The coupling mechanism according to claim 11, wherein the detachable snap clip comprises:

a base;

a head that extends from the base in a hook shape, is resiliently deflectable, and is configured to couple to one cylindrical structure of the holding mechanism; and a notch on the end of the head.

13. The coupling mechanism according to claim 11, wherein the detachable snap clip is configured to couple to the inventory divider via a base comprising:

two substantially parallel members;

one or more protrusions extending inwardly within a space between the two substantially parallel members, wherein the protrusions have a tapered outer surface profile and each protrusion is configured to engage a hole in the inventory divider; and one or more recessed portions disposed opposite to the protrusions.

* * * * *